US00PP34298P2

(12) United States Plant Patent
Hansen

(10) Patent No.: US PP34,298 P2
(45) Date of Patent: Jun. 7, 2022

(54) ***BUDDLEIA* PLANT NAMED 'VIOLET CASCADE'**

(50) Latin Name: *Buddleia davidii*
Varietal Denomination: Violet Cascade

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/803,082

(22) Filed: Feb. 1, 2022

(51) Int. Cl.
*A01H 6/00* (2018.01)
*A01H 5/02* (2018.01)

(52) U.S. Cl.
USPC ..... Plt./242

(58) Field of Classification Search
USPC ..... Plt./242
See application file for complete search history.

*Primary Examiner* — Annette H Para

(57) ABSTRACT

The new and distinct plant of *Buddleia* 'Violet Cascade' is a rounded-mounded, multi-stemmed, winter-hardy butterfly bush with very long, narrow, outwardly drooping flowering thyrse producing a waterfall effect over a long season beginning mid-summer with sweetly-fragrant flowers of deep purple petals and orangish-yellow eyes that are attractively offset by dark green foliage with silvery undersides. No seed has been observed since development. The new plant is valuable for landscaping en masse, as an accent or as a potted specimen.

1 Drawing Sheet

Botanical classification: *Buddleia davidii.*
Variety denomination: 'Violet Cascade'.

STATEMENT REGARDING PRIOR DISCLOSURES UNDER 37 CFR 1.77(B)(6)

The first public disclosure of the claimed plant, in the form of a sale, was made by Walters Gardens, Inc. on Aug. 23, 2021 to Centerton Nursery, Inc. Prior to that, on Feb. 1, 2021 the claimed plant was displayed with a non-enabling photograph and brief description in a website operated by Walters Gardens, Inc., and on May 21, 2021 as a non-enabling photograph and brief description in the 2021-2022 Catalog by Walters Gardens, Inc., who obtained the plant and all information relating thereto, from the inventor. No plants of *Buddleia* 'Violet Cascade' were in condition to sell prior to the first sale date, nor have been sold, in this country or anywhere in the world, nor has any disclosure of the new plant been made more than one year prior the filing date of this application, and such sale or disclosure within one year was either derived directly or indirectly from the inventor.

BACKGROUND OF THE PLANT

The present invention relates to the new and distinct butterfly bush plant of the Scrophulariaceae family, *Buddleia* 'Violet Cascade' hybridized by Hans A. Hansen on Jun. 23, 2016 at a wholesale perennial nursery in Zeeland, Mich., USA. 'Violet Cascade' is the result of an ongoing breeding program conducted by the inventor. The goals for this program have been to produce improved, garden-worthy plants for the ornamental plant market. The new plant, assigned the breeder code 16-6-1 toward the end of the evaluation trials, was the result of a cross between the unreleased proprietary hybrid known by the breeder code 14-18-2 (not patented) as the female or seed parent. The male parent was the unreleased proprietary hybrid named by the breeder code 14-18-3 (not patented). The new cultivar was selected as single individual flowering plant within the progeny of the above cross at the same nursery in Zeeland, Mich.

*Buddleia* 'Violet Cascade' was first asexually propagated from a single select plant in 2019 by stem cuttings at the same nursery in Zeeland, Mich. The resultant asexually propagated plants have been found to be stable and true to type in successive generations of asexual reproduction.

SUMMARY OF THE INVENTION

Plants of the new *Buddleia* have not been observed under all possible environmental conditions. The phenotype may vary somewhat with variations in environment and cultural practices such as temperature, light intensity, available moisture and nutrition without, however, any variance in genotype.

In comparison to the new plant, the female parent has lighter colored flowers, the habit was more open and the thyrse is more branched at the base. The male flower has a more open habit, the flowers are lighter colored, and the thyrse is more branched at the base. Both parents were fertile.

The nearest comparison plants known to the inventor are: 'Wisteria Lane' U.S. Plant Pat. No. 27,833, 'Grand Cascade' U.S. Plant Pat. No. 30,868, 'Lavender Cascade' U.S. Plant Pat. No. 30,624, 'Lavender Cupcake' U.S. Plant Pat. No. 28,221, 'Blue Knight' U.S. Plant Pat. No. 28,178 and 'Dartmoor' (not patented).

'Wisteria Lane' is significantly shorter in habit with smaller thyrse, the branches are more drooping instead of mainly the thyrses drooping and the petals are light purple. 'Grand Cascade' is larger in habit and has longer and broader thyrse with petals that are light lavender-purple colored. 'Lavender Cascade' has taller and broader habit, the flower petals that are pale lilac and the thyrse is broader and held more horizontally and less drooping. 'Lavender Cupcake' has a more upright thyrse, the flower color is light lavender purple and the thyrse is much shorter. 'Blue Knight' has a smaller habit, with shorter stockier thyrse of light lavender flowers that darken to blue-purple and the foliage is more silvery. 'Dartmoor' has a taller and broader habit with shorter thyrses that are more branched at the base and the flowers are medium purple-colored. 'Lavender Cascade' is the only other comparison plant of the above group that has not shown any seed development; all the others produce seed.

*Buddleia* 'Violet Cascade' is a unique winter-hardy butterfly bush different from all other *Buddleia* cultivars known to the inventor based on the following combined repeatedly observed distinguishing traits:

1. Winter-hardy butterfly bush shrub, with multiple-stemmed, well-branched, rounded, horizontal to arching, mounded habit;
2. Large, dense, narrow, many-flowered, elongated and horizontal to outwardly-drooping thyrse flowering over a prolonged season beginning mid-summer;
3. Flowers with deep purple petals and orangish-yellow eye;
4. Lanceolate foliage of dark green with silvery undersides;
5. No seed production has been observed since development.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
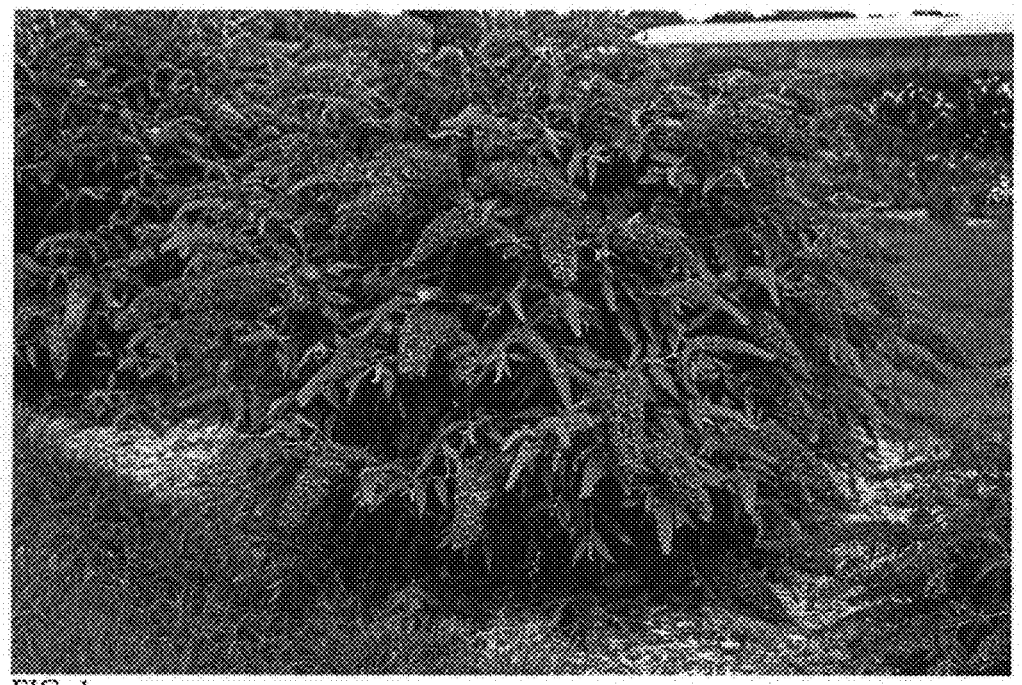
FIG. 1 shows the habit of a four-year-old plant in mid-season flowering.
Figure 2:
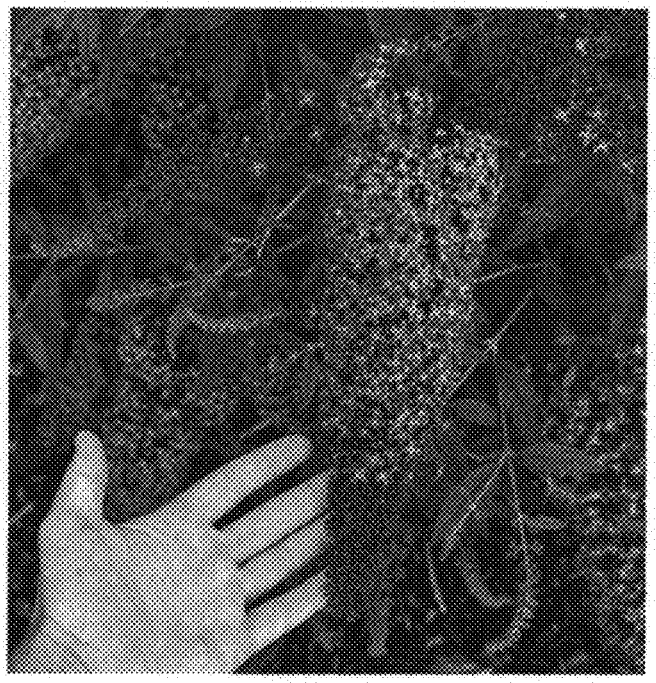
FIG. 2 shows a close-up of the inflorescence.

The following descriptions and color references are based on the 2015 edition of The Royal Horticultural Society Colour Chart except where common dictionary terms are used. The new plant, *Buddleia* 'Violet Cascade', has not been observed under all possible environments. The phenotype may vary slightly with different environmental conditions, such as temperature, light, fertility, moisture and maturity levels, but without any change in the genotype. The following observations and size descriptions are of four-year-old plants in the loamy-sand, open-sun, display garden of a nursery in Zeeland, Mich. with supplemental fertilizer and water as needed. The plants are natural habit and were not treated with plant growth regulators, nor were they pinched at any time in the growth year except to cut back woody stems to about 15 cm tall in early spring.

Parentage: Unreleased proprietary hybrid 14-18-2 as the female or seed patent; the male or pollen parent was the unreleased, proprietary, hybrid known by 14-18-3;

Propagation:

*Method*.—Softwood shoot cuttings.

*Time to initiate roots from tissue culture*.—About two weeks.

*Rooting habit*.—Normal, dense and branching, developing thick at base to about 1.5 cm diameter.

*Root color*.—Creamy white between RHS 159A and lighter than RHS 159 D depending on soil type.

*Crop time*.—Under normal summer growing conditions 12 to 15 weeks to flower in a four-liter container from cutting. Plant vigor is very good.

Plant description:

*Plant shape and habit*.—Winter-hardy, herbaceous to semi-woody, well-branched shrub with about 34 moderately thick upright and branched main stems producing a rounded mound, to about 122 cm tall and about 210 cm wide.

*Stem*.—Terete and woody in lower portion, with exfoliating bark; younger upper portion tomentose to tomentulose; strong and flexible, horizontal to arching in terminal thyrse; average about 90 cm long from soil line to just below terminal flowers, and about 15.0 mm diameter at the base; about 14 branches per main stem before distal flowers in upper 7 nodes, extending at about 50° angle from perpendicular main stem.

*Stem color*.—Young distal portion just below flowers nearest RHS 148D; basal 15 cm with striations of nearest RHS 156CD and nearest RHS 197C.

*Internode*.—About 14 nodes per main stem below terminal thyrse, average internode length about 6.5 cm on unpinched plant; upper internodes slightly more elongated than lower internodes.

Foliage description: Opposite; lanceolate; decussate; serrate with about 5 teeth per cm, teeth about 0.5 mm long and 2.0 mm wide; glabrous and dull adaxial; micro-farinose argenteous abaxial; attenuate base; narrowly acute apex; no foliar fragrance detected;

*Leaf blade size*.—Up to about 14.4 cm long and about 3.9 cm wide, average about 12.0 cm long and about 3.0 cm wide; becoming smaller in distal portion of stem.

*Foliage color*.—Young expanding leaf adaxial distally between RHS NN173A and RHS 139A, proximally nearest RHS N138B, young expanding abaxial nearest RHS 191D; mature leaves adaxial nearest and RHS NN137A, mature abaxial between RHS 195B and RHS 195A.

*Veins*.—Reticulate; abaxial costate and farinose when young becoming micro-farinose with maturity; adaxial glabrous, slightly impressed.

*Vein color*.—Adaxial midrib and secondary veins nearest RHS NN137B, abaxial midrib nearest RHS 148D and secondary veins nearest RHS 147B.

*Petioles*.—Short; micro-farinose; concavo-convex; to about 9.0 mm long and 3.0 mm wide.

*Petiole color*.—Adaxial nearest RHS 138B; abaxial nearest RHS 148D.

*Inflorescence description*.—Glomerate densely-branched thyrse consisting of up to about 3,000 self-cleaning salverform flowers, average about 2,200 flowers per inflorescence; with up to about 44 branches; to about 35 cm long and 14 cm wide at base; average about 25 cm long and 12.5 cm wide; beginning in mid-July and continuing until frost in Michigan; thyrse effective for about three weeks.

*Inflorescence attitude*.—Outwardly to slightly drooping.

*Flower buds one day prior to opening*.—Elongated clavate, apex rounded; glabrous except micro-puberulent abaxial corolla tube; about 13.0 mm long, about 3.0 mm diameter in club, tube about 1.0 mm diameter and about 11.0 mm long.

*Flower bud color*.—Nearest RHS N82B in club portion, tube nearest RHS 79C with calyx nearest RHS 138B in middle with fusion lines nearest RHS N82A.

*Calyx*.—Campanulate; 3.0 mm long and 1.0 mm diameter at apex.

*Sepals*.—Typically four; adpressed to corolla tube; acute apex; glabrous adaxial and glabrous to micro-puberulent abaxial; margin entire; fused in about the basal 2.0 mm and split in about the terminal 1.0 mm, individually about 0.8 mm wide at point of fusion.

*Sepal color*.—Variable; nearest RHS 138B in middle with fusion lines nearest RHS N82A.

*Flowers*.—Salverform; actinomorphic; perfect; to about 16.0 mm long and 7.0 mm wide naturally at face and 11.5 mm wide with petals flattened; with straight terete tube about 12.0 mm long and 1.5 mm diameter at base and 2.5 mm wide before face, and opening to slightly cupped face about 3.0 mm deep; attitude outward from thyrse center; remaining on the thyrse and effective for about five to seven days.

*Flowers fragrance*.—Pleasantly and distinctly honey sweet.

*Petals*.—Typically four; blade rounded with crenate margin; apex rounded; base fused into corolla tube; blades glabrous adaxial and abaxial; tube micro-puberulent abaxial and puberulent in distal two-thirds and glabrous in proximal one-third; blade to about 4.5 mm across and about 4.5 mm long from throat to apex.

*Petal color*.—Upon opening adaxial face nearest RHS N82A, when fully open at maturity nearest RHS N87A, eye nearest RHS 23A; abaxial face blade upon opening between RHS N82B and RHS N82A, when fully open at maturity nearest RHS N82A; adaxial tube upon opening distally near face nearest RHS 23B, proximally nearest RHS 160C; adaxial tube fully open distally nearest RHS 167A, proximally nearest RHS 145D; abaxial tube basal 2 mm nearest RHS 145D, just after opening distal portion nearest RHS N79D and at maturity distal portion nearest RHS N77A.

*Gynoecium*.—Pistil: one; about 4.0 mm long. Style: glabrous, glutinous, ellipsoidal; about 1.0 mm long and about 0.2 mm diameter; color nearest RHS 145D; Stigma: narrow ellipsoidal, minutely puberulent; about 0.3 mm in diameter and about 1.0 mm long; color nearest RHS 146C; Ovary: superior; ellipsoidal, rounded apex and base; about 2.0 mm long and about 0.7 mm diameter; rounded apex and base; color nearest RHS 145D.

*Androecium*.—Typically four; adnate to inner corolla tube. Filaments: adnate to inner corolla tube for about 5.5 mm; free in distal 0.1 mm long and less than 0.1 mm diameter; adnate to proximal adaxial corolla tube; color same as inner corolla where attached and free portion nearest RHS 85D; Anthers: typically four; ellipsoidal; introrse; about 1.5 mm long and 0.3 mm wide; color nearest RHS 163C; Pollen: not observed.

*Pedicel*.—Short; micro-puberulent; about 1.5 mm long and about 0.5 mm diameter; color nearest RHS N77A.

*Peduncle*.—Cylindrical to angular, lightly carinate to striate; micro-puberulent to micro-farinose; to about 31.0 cm long and about 3.5 mm across at base below flowers.

*Peduncle color*.—Nearest RHS 147B.

*Fruit and seed*.—Not observed in any trial conditions in four years of observations; fecundity or sterility not completely assessed.

Disease resistance: Resistance has been noted to deer browsing. Other pest and disease resistance beyond that common to butterfly bush cultivars has not been observed. The plant grows best with plenty of moisture and adequate drainage, but is able to tolerate some drought when mature.

Hardiness: At least from USDA zone 5 through 10 with some occasional stem dieback.

It is claimed:

1. A new cultivar of winter-hardy butterfly bush plant named *Buddleia* 'Violet Cascade' as herein illustrated and described.

* * * * *